United States Patent
Harvey

(10) Patent No.: US 10,047,309 B1
(45) Date of Patent: Aug. 14, 2018

(54) HIGH DENSITY FUELS GENERATED BY CATALYTIC CYCLOADDITION

(71) Applicant: THE UNITED STATES OF AMERICA as represented by the SECRETARY of the NAVY, Washington, DC (US)

(72) Inventor: Benjamin G Harvey, Ridgecrest, CA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 15/176,870

(22) Filed: Jun. 8, 2016

(51) Int. Cl.
*C10L 1/16* (2006.01)
*C10L 1/04* (2006.01)
*C07C 2/42* (2006.01)

(52) U.S. Cl.
CPC .............. *C10L 1/1608* (2013.01); *C07C 2/42* (2013.01); *C10L 1/04* (2013.01); *C10L 2290/24* (2013.01); *C10L 2290/38* (2013.01)

(58) Field of Classification Search
CPC .. C07C 5/03; C07C 11/02; C07C 2/16; C07C 2/34; C07C 9/14; C07C 9/22; C07C 2527/054; C07C 2531/14; C07C 2531/38; C07C 2/42; C10G 2400/08; C10G 2400/20; C10G 2400/22; C10G 3/42; C10G 3/44; C10G 50/00; C10G 69/126; C10G 2300/4037; C10G 45/00; C10G 45/58; C10G 45/60; C10G 45/62; C10G 45/70; C10G 65/043; Y02P 30/20; C10L 1/04; C10L 1/08; C10L 1/1608; C10L 2290/38; C10L 2290/24
See application file for complete search history.

(56) References Cited

U.S. PATENT DOCUMENTS

2015/0011810 A1* 1/2015 Harvey ..................... C10L 1/04
585/22

OTHER PUBLICATIONS

Chong D. et al. Cycloaddition Reactions of Unactivated Olefins Catalyzed by an Organorhenium Electron-Transfer Mediator. Journal of American Chemical Society. May 2009. pp. 7968-7969.*

* cited by examiner

*Primary Examiner* — Latosha Hines
(74) *Attorney, Agent, or Firm* — Charlene A. Haley

(57) ABSTRACT

A method for making high density fuels including, providing pure cyclic hydrocarbons or a mixture of cyclic hydrocarbons, subjecting the cyclic hydrocarbons or mixture of cyclic hydrocarbons to electrochemical cycloaddition in the presence of at least one catalyst to generate multicyclic oligomers, and purifying the multicyclic oligomer to yield a high density fuel.

20 Claims, 1 Drawing Sheet wherein "n" and "m" are integers in the range of about 0-4;

wherein "R" is an alkyl group; and wherein "x" is an integer in the range of 0 to n+2 and "y" is an integer in the range of 0 to m+2.

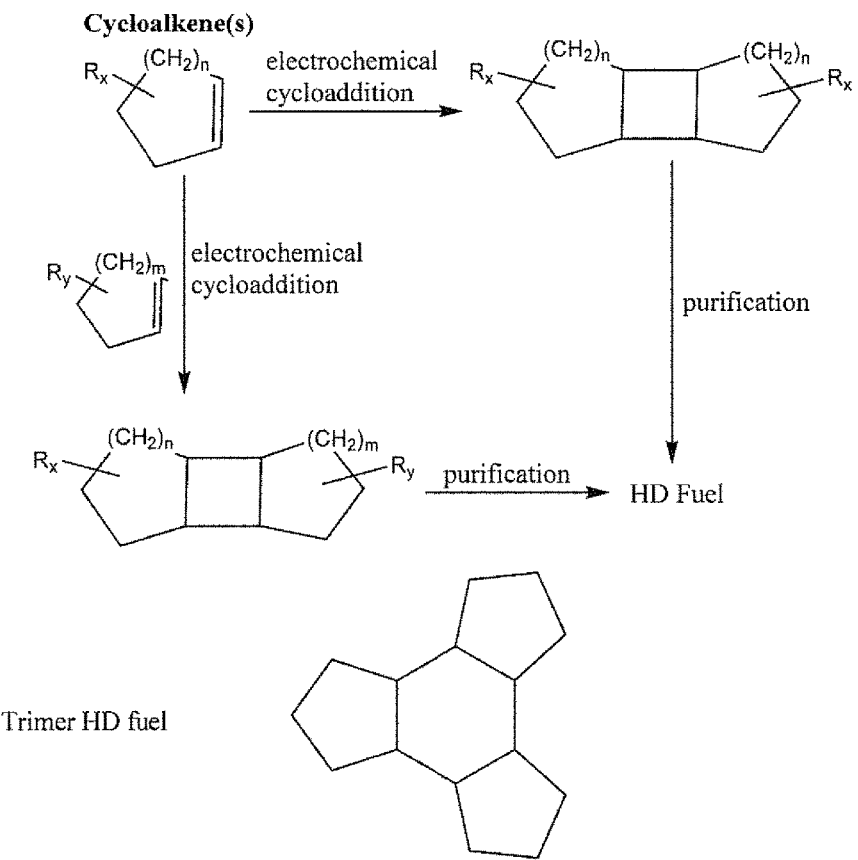
wherein "n" and "m" are integers in the range of about 0-4;
wherein "R" is an alkyl group; and
wherein "x" is an integer in the range of 0 to n+2 and "y" is an integer in the range of 0 to m+2.

HIGH DENSITY FUELS GENERATED BY CATALYTIC CYCLOADDITION

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to high density tactical fuels having the potential to increase the range and or loiter time for a variety of Navy platforms. Embodiments of the invention describe an atom efficient electrochemical method to convert low value feedstocks into high-density multicyclic fuels.

BRIEF DESCRIPTION OF THE DRAWING

FIG. 1 is a chemical flow chart of cyclic hydrocarbons undergoing electrochemical eycloaddition in the presence of a catalyst to generate a multicyclic oligomer to produce a high density fuel, according to embodiments of the invention.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF THE EMBODIMENTS OF THE INVENTION

Embodiments of the invention generally relate to methods for generating high density fuels via electrochemical cycloaddition of cyclic alkenes in the presence of a catalyst to generate a multicyclic oligomer Further embodiments of the invention describe a method for the efficient coupling of cyclic alkenes to form multicyclic hydrocarbon fuels with densities in excess of 0.85 g/mL and net heats of combustion greater than 130,000 btu/gal.

The high-performance tactical fuel JP-10 is synthesized by thermal cracking of napthenic oils to generate cyclopentadiene which is then isolated and thermally dimerized to dicyclopentadiene, hydrogenated to tetrahydrodicyclopentadiene, and then isomerized to exo-tetrahydrodicyclopentadiene. Thus, the synthesis of JP-10 requires six steps. This complexity is reflected in the much higher acquisition cost of JP-10 compared to conventional fuels. In contrast, the current invention describes an electrochemical method that can generate fuels with densities and net heats of combustion similar to JP-10 in one step from either pure cyclic alkenes or complex mixtures of cyclic alkenes. The cycloaddition of cyclic alkenes using an organorhenium catalyst is described in Chong, D.; Stewart, M.; Geiger, W. E. J. Am. Chem. Soc. 2009, 131, 7968-7969.

1. A pure cyclic hydrocarbon or mixture of cyclic hydrocarbons is derived from petroleum or a renewable source.

2. The cyclic hydrocarbon(s) undergoes electrochemical cycloaddition in the presence of a catalyst to generate an oligomer (dimer or trimer).

3. The multicyclic oligomer is purified to yield a high density fuel.

Embodiments include the following process:

1. A cyclic olefin with a parent ring system including cyclopentene, cyclohexene, cycloheptene, or cyclooctene is used as the substrate. In embodiments, the ring can be functionalized at one or more positions. In embodiments, the cyclic olefin is derived from a renewable source. In embodiments, the cyclic olefins are terpenoids. Some of the renewable sources include, but are not limited to, lignocellulosic biomass, cyclic alkenes generated biosynthetically from biomass sugars or lignin, pine resin, and turpentine. In embodiments, a mixture of two different cyclic olefins is used. In embodiments, a complex mixture of multiple cyclic olefins is used. In embodiments, the pure cyclic alkenes are selected from the group consisting of cyclopentene, cyclohexene, cycloheptene, or cyclooctene or said mixture of cyclic hydrocarbons is a mixture of two or more different cyclic olefins. In embodiments, the rings of the cyclic olefins or said mixture of cyclic olefins are functionalized at one or more positions. In embodiments, the cyclic olefins are diluted in a first solvent including methylene chloride, acetonitrile, alkyl carbonates, DMSO, ionic liquids including 1-ethyl-3-methylimidazolium bis(trifluoromethylsulfonyl)imide, 1-ethyl-3-methyl imidazolium trifluoromethanesulfonate, 1-butyl-1-methylpyrrolidinium bis(trifluoromethylsulfonyl) imide, 1-hexyl-3-methylimidazolium, 1-ethyl-3-methylimidazolium dicyanamide, and 11-methyl-3-octylimidazolium tetrafluoroborate and related ionic liquids. In embodiments, the cyclic olefins are diluted in a second hydrocarbon solvent including alkanes, cycloalkanes, benzene, toluene, other alkyl aromatics. In embodiments, the cyclic olefins are diluted in a petroleum-based or renewable fuel.

2. The cyclic olefin(s) are dissolved in a solvent including an electrolyte in the presence of a catalyst that facilitates the cycloaddition of the olefin to generate a multicyclic oligomer. In embodiments, the solvent is an ionic liquid. In embodiments, the catalyst is an organorhenium compound. In embodiments, the reaction is biphasic with the organic (cyclic olefin phase) having limited solubility in the solvent/electrolyte solution. In embodiments, the electrolyte/catalyst mixture is recycled. Catalysts include, but are not limited to: transition metal based organometallic compounds that reversibly generate radical cations to facilitate one-electron oxidation of unactivated cyclic alkenes. In other embodiments the metals are bound to organic ligands that enhance the stability of the radical species. A specific example of an active catalyst is the radical cation $[CpRe(CO)3]^+$. Other catalysts can be generated from organometallic complexes of other transition metals including, but not limited to, Mn, Co, Rh, Ir, Fe, Ru, Cr, Mo, and W. Suitable electrolytes include salts having weakly coordinating anions (e.g. $[B(C_6F_5)_4]^-$). In the case of ionic liquids, no additional electrolyte is required.

3. The multicyclic oligomer(s) is purified to yield a high density fuel. In embodiments, the oligomer(s) is separated by distillation. In embodiments, the oligomer(s) is obtained as a component of a complex mixture. In embodiments, the biphasic reaction product is separated by decantation.

FIG. 1 shows a chemical flow chart of cyclic hydrocarbons undergoing electrochemical cycloaddition in the presence of a catalyst to generate a multicyclic oligomer to produce a high density fuel.

The embodiments of the invention generally relate to methods for making high density fuels including, providing pure cyclic alkenes or a mixture of cyclic alkenes;

subjecting said cyclic alkenes or said mixture of cyclic alkenes to electrochemical cycloaddition in the presence of at least one catalyst to generate multicyclic oligomers; and purifying said multicyclic oligomer to yield a high density fuel;

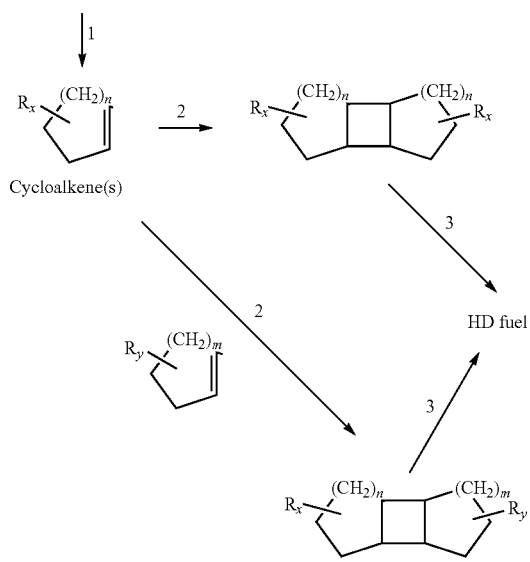

Cycloalkene(s)

HD fuel and timer HD fuels;

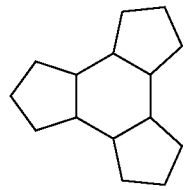 [SMILES: C1CC2C3CCCC3C3CCCC3C2C1]

wherein "n" and "m" are integers in the range of about 0-4;

wherein "R" is an alkyl group; and wherein "x" is an integer in the range of 0 to n+2 and "y" is an integer in the range of 0 to m+2. The electrochemical cycloaddition process takes place in the presence of a potential.

Embodiments further include dissolving or mixing the cyclic olefin(s) in at least one first solvent including at least one electrolyte in the presence of the catalyst that facilitates the cycloaddition of the cyclic olefin(s) to generate the multicyclic oligomers. In embodiments, the first solvent is an ionic liquid including 1-ethyl-3-methylimidazolium bis(trifluoromethylsulfonyl)imide, 1-ethyl-3-methylimidazolium trifluoromethanesulfonate, 1-butyl-1-methylpyrrolidinium bis(trifluoro methylsulfonyl)imide, 1-hexyl-3-methylimidazolium, 1-ethyl-3-methylimidazolium dicyanamide, 11-methyl-3-octylimidazolium tetrafluoroborate and related ionic liquids. In embodiments, the catalyst is an organorhenium compound.

In embodiments, the reaction is biphasic with the organic (cyclic alkene phase) having limited solubility in the solvent/electrolyte mixture. The cyclic alkene is added to the first solvent/electrolyte mixture. It can either be soluble or slightly soluble (two phases). When it is slightly soluble it can be mechanically separated from the mixture after the reaction is complete. In embodiments, the electrolyte/catalyst mixture is recycled by mechanically separating the cyclic alkene phase. In embodiments, the multicyclic oligomers are dimers or trimers. In embodiments, the multicyclic oligomer(s) is separated by distillation. In other embodiments, the multicyclic oligomer(s) is obtained as a component of a complex mixture. In yet other embodiments, the multicyclic oligomer(s) is a component of a biphasic system that is separated by decantation.

Another aspect of the invention relates to high density fuels produced by the methods herein;

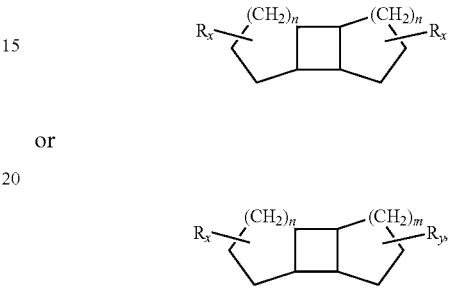

or and any combination thereof;

wherein "n" and "m" are integers in the range of about 0-4;

wherein "R" is an alkyl group; and wherein "x" is an integer in the range of 0-n+2 and "y" is an integer in the range of 0 to m+2.

In embodiments, the high density fuels have densities greater than 0.85 g/mL and net heats of combustion greater than 130,000 Btu/gal.

PROPHETIC EXAMPLES

Prophetic examples are for illustration purposes only and not to be used to limit any of the embodiments.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A method for making high density fuels, comprising:
   providing pure cyclic alkenes or a mixture of cyclic alkenes;

subjecting said cyclic alkenes or said mixture of cyclic alkenes to electrochemical cycloaddition in the presence of at least one catalyst to generate multicyclic oligomers; and purifying said multicyclic oligomer to yield a high density fuel;

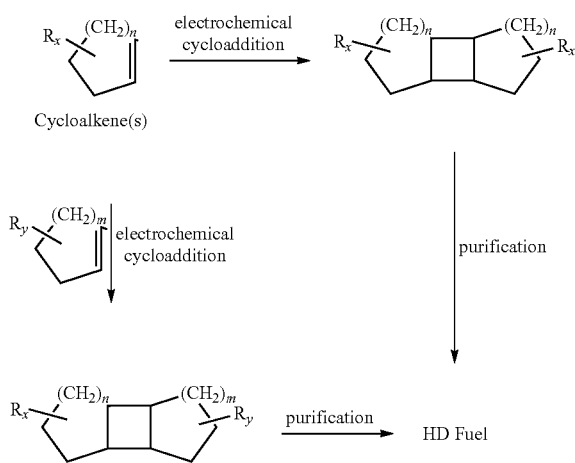

wherein "n" and "m" are integers in the range of about 0-4;

wherein "R" is an alkyl group;

wherein "x" is an integer in the range of 0 to n+2 and "y" is an integer in the range of 0 to m+2; and, wherein x+y is at least 1.

2. The method according to claim 1, wherein said pure cyclic alkenes are selected from the group consisting of cyclopentene, cyclohexene, cycloheptene, or cyclooctene or said mixture of cyclic hydrocarbons is a mixture of two or more different cyclic olefins.

3. The method according to claim 2, wherein said cyclic alkenes are terpenoids.

4. The method according to claim 2, wherein the rings of said cyclic alkenes or said mixture of cyclic alkenes are functionalized at one or more positions.

5. The method according to claim 2, further comprising diluting said cyclic alkenes in at least one first solvent including methylene chloride, acetonitrile, DMSO, ionic liquids including 1-ethyl-3-methylimidazolium bis(trifluoromethylsulfonyl)imide, 1-ethyl-3-methylimidazolium trifluoromethanesulfonate, 1-butyl-1-methylpyrrolidinium bis(trifluoromethylsulfonyl)imide, 1-hexyl-3-methylimidazolium, 1-ethyl-3-methylimidazolium dicyanamide, and 11-methyl-3-octylimidazolium tetrafluoroborate and related ionic liquids; wherein said at least one first solvent is not Lewis acidic.

6. The method according to claim 2, further comprising diluting said cyclic alkenes in at least one second solvent including alkanes, cycloalkanes, benzene, toluene, and other alkyl aromatics.

7. The method according to claim 2, further comprising diluting said cyclic alkenes in a petroleum-based or renewable fuel.

8. The method according to claim 5, further comprising dissolving or mixing said cyclic alkene(s) in said at least one first solvent including at least one electrolyte in the presence of said catalyst that facilitates said cycloaddition of said cyclic alkene(s) to generate said multicyclic oligomers.

9. The method according to claim 5, wherein said first solvent is an ionic liquid including 1-ethyl-3-methylimidazolium bis(trifluoromethylsulfonyl)imide, 1-ethyl-3-methylimidazolium trifluoromethanesulfonate, 1-butyl-1-methylpyrrolidinium bis(trifluoro methylsulfonyl)imide, 1-hexyl-3-methylimidazolium, 1-ethyl-3-methylimidazolium dicyanamide, and 11-methyl-3-octylimidazolium tetrafluoroborate and related ionic liquids.

10. The method according to claim 1, wherein said catalyst is a transition metal based organometallic compound that reversibly generates radical cations to facilitate one-electron oxidation of unactivated cyclic alkenes.

11. The method according to claim 1, wherein said catalyst is a radical cation.

12. The method according to claim 1, wherein said catalyst is an organorhenium compound.

13. The method according to claim 8, wherein said reaction is biphasic with the organic phase (cyclic alkene phase) having limited solubility in the solvent/electrolyte mixture.

14. The method according to claim 13, wherein said electrolyte/catalyst mixture is recycled by mechanically separating said cyclic alkene phase.

15. The method according to claim 1, wherein said multicyclic oligomers are dimers or trimers.

16. The method according to claim 1, wherein said multicyclic oligomer(s) is separated by distillation.

17. The method according to claim 1, wherein said multicyclic oligomer(s) is obtained as a component of a complex mixture.

18. The method according to claim 1, wherein said multicyclic oligomer(s) is a biphasic system that is separated by decantation.

19. The method according to claim 1, wherein said high density fuels have densities greater than 0.85 g/mL and net heats of combustion greater than 130,000 Btu/gal.

20. The method according to claim 15, wherein said trimer is

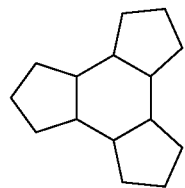 [SMILES: C1CC2C3CCCC3C3CCCC3C2C1]

* * * * *